(12) United States Patent
Yu et al.

(10) Patent No.: US 11,522,314 B2
(45) Date of Patent: Dec. 6, 2022

(54) BASE AND DETECTION APPARATUS

(71) Applicant: Anhui Huami Information Technology Co., Ltd., Anhui (CN)

(72) Inventors: Pengtao Yu, Anhui (CN); Lian Zhang, Anhui (CN); Zhongda Guan, Anhui (CN)

(73) Assignee: Anhui Huami Information Technology Co., Ltd., Anhui (CN)

( * ) Notice: Subject to any disclaimer, the term of this patent is extended or adjusted under 35 U.S.C. 154(b) by 1182 days.

(21) Appl. No.: 16/034,092

(22) Filed: Jul. 12, 2018

(65) Prior Publication Data
US 2018/0323540 A1 Nov. 8, 2018

Related U.S. Application Data

(63) Continuation of application No. PCT/CN2018/078055, filed on Mar. 5, 2018.

(30) Foreign Application Priority Data

Mar. 8, 2017 (CN) .......................... 201720221622.6

(51) Int. Cl.
*H01R 13/627* (2006.01)
*H04B 1/3827* (2015.01)
(Continued)

(52) U.S. Cl.
CPC ........... *H01R 13/6273* (2013.01); *A61B 5/00* (2013.01); *A61B 5/681* (2013.01); *H01R 33/05* (2013.01);
(Continued)

(58) Field of Classification Search
CPC ..... A61B 5/0015; A61B 5/6838; A61B 5/002; A61B 5/02438; A61B 5/0245; A61B 5/00;
(Continued)

(56) References Cited

U.S. PATENT DOCUMENTS

| | | | | |
|---|---|---|---|---|
| 8,243,453 | B2 * | 8/2012 | Van Dijk | H02B 1/56 218/120 |
| 8,276,298 | B2 * | 10/2012 | Padgett | A44C 5/0069 63/3.2 |
| 8,590,192 | B2 * | 11/2013 | Padgett | A44C 5/0069 63/3.2 |
| 8,758,241 | B2 * | 6/2014 | Charles, Jr. | G06F 1/163 361/728 |

(Continued)

FOREIGN PATENT DOCUMENTS

CN 204682716 U 10/2015
CN 105411563 A 3/2016
(Continued)

OTHER PUBLICATIONS

International Search Report for International Application No. PCT/CN2018/078055 dated Mar. 30, 2018.

*Primary Examiner* — Gary F Paumen
(74) *Attorney, Agent, or Firm* — Young Basile Hanlon & MacFarlane, P.C.

(57) ABSTRACT

A base and a detection device for installing a detection apparatus are provided. The base includes a base member, a first fixing member, provided on the base member for fixing the detection apparatus, and an extension member, configured to transmit an electric signal to the detection apparatus, in which the extension member extends outward to a predetermined position of the base member. The detection device includes a detection apparatus and the base.

20 Claims, 4 Drawing Sheets

(51) Int. Cl.

| | |
|---|---|
| *H01R 33/05* | (2006.01) |
| *A61B 5/00* | (2006.01) |
| *H01R 4/04* | (2006.01) |
| *A61B 5/25* | (2021.01) |
| *A61B 5/259* | (2021.01) |
| *A61B 5/282* | (2021.01) |

(52) U.S. Cl.
CPC ............ *H04B 1/385* (2013.01); *A61B 5/25* (2021.01); *A61B 5/259* (2021.01); *A61B 5/282* (2021.01); *A61B 2560/045* (2013.01); *A61B 2562/0209* (2013.01); *H01R 4/04* (2013.01); *H01R 2201/12* (2013.01); *H01R 2201/20* (2013.01)

(58) Field of Classification Search
CPC .......... A61B 5/681; A61B 5/25; A61B 5/259; A61B 5/282; A61B 2562/0209; A61B 2560/045; H01R 13/6273; H01R 33/05; H01R 2201/20; H01R 4/04; H04B 1/385
USPC .......................................................... 439/37
See application file for complete search history.

(56) References Cited

U.S. PATENT DOCUMENTS

| | | | |
|---|---|---|---|
| 9,579,021 B2* | 2/2017 | Chang ................ | A61B 5/0015 |
| 2005/0048804 A1* | 3/2005 | Henriet ................ | H01Q 1/273 |
| | | | 439/37 |
| 2010/0137701 A1* | 6/2010 | Papastefanou ......... | G01D 11/24 |
| | | | 2/170 |
| 2014/0218852 A1* | 8/2014 | Alcazar ................ | G06F 1/1635 |
| | | | 361/679.03 |
| 2015/0296963 A1* | 10/2015 | Byun .................... | G04G 17/08 |
| | | | 224/191 |
| 2016/0091921 A1* | 3/2016 | Lee ........................ | G06F 1/163 |
| | | | 250/372 |
| 2016/0278702 A1* | 9/2016 | Chen ...................... | A61B 5/24 |
| 2018/0294554 A1* | 10/2018 | Xu ........................ | A44C 5/0053 |

FOREIGN PATENT DOCUMENTS

| | | |
|---|---|---|
| CN | 205267221 U | 6/2016 |
| CN | 205493818 U | 8/2016 |
| CN | 106037173 A | 10/2016 |
| CN | 205728439 U | 11/2016 |

\* cited by examiner

BASE AND DETECTION APPARATUS

CROSS-REFERENCE TO RELATED APPLICATION(S)

This application is a continuation of International Application No. PCT/CN2018/078055, filed on Mar. 5, 2018, which claims priority to Chinese Patent Application No. 201720221622.6, filed on Mar. 8, 2017, the contents of both of which are hereby incorporated by reference in their entireties.

TECHNICAL FIELD

This disclosure relates to a base and a detection apparatus.

BACKGROUND

Some health detection devices (e.g., a smart wristband) have a compact structure and can be made into a wearable device to be worn by an individual. Such a wearable device can have a detection apparatus, which can be detached from other fixed parts of the wearable devices and run independently.

For example, a smart wristband can include a detection apparatus and a wristband installed at both ends of the detection apparatus. The detection apparatus can be worn by the individual through the wristband. The detection apparatus can have functions such as, for example, a pedometer, an alarm, sleep monitoring, health management, anti-lost positioning, or heart rate detection. After the wristband is removed from the detection apparatus, the function of the detection apparatus is not affected.

The detection apparatus needs to meet wearable requirements, and therefore is small in size. When the individual needs to detect a large body part, such as the heart area, the detection apparatus may not be suitable.

SUMMARY

A base and a detection device are provided in this disclosure.

In an aspect, a base for installing a detection apparatus is provided. The base includes a base member, a first fixing member, provided on the base member for fixing the detection apparatus, and an extension member, configured to transmit an electric signal to the detection apparatus, wherein the extension member extends outward to a predetermined position of the base member.

In another aspect, a detection device is provided. The device includes a detection apparatus and a base. The base includes a base member, a first fixing member, provided on the base member for fixing the detection apparatus, and an extension member, configured to transmit an electric signal to the detection apparatus, wherein the extension member extends outward to a predetermined position of the base member.

In another aspect, a detection device is provided. The device includes a detection apparatus, a wristband, and a base. The base includes a base member, a first fixing member, provided on the base member for fixing the detection apparatus, and an extension member, configured to transmit an electric signal to the detection apparatus, wherein the extension member extends outward to a predetermined position of the base member.

BRIEF DESCRIPTION OF THE DRAWINGS

This disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
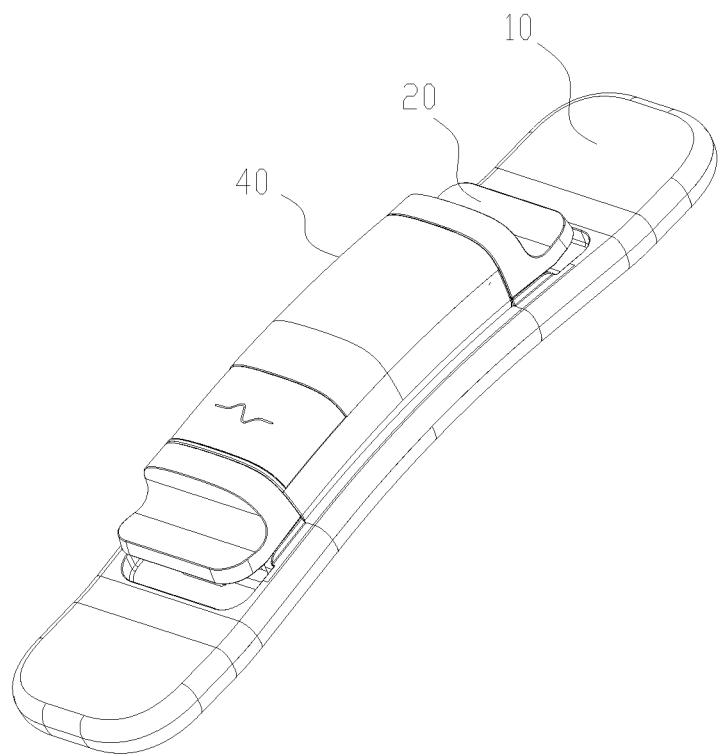
FIG. 1 is a diagram of structures of a detection device according to an implementation of this disclosure.

The parts and corresponding reference numerals used in the following description and FIGS. 1-6 include a base member 10, an arcuate portion 11, a contact portion 12, a first fixing member 20, a clamp member 21, an elastic element 22, a clip member 23, an elastic portion 231, a holding portion 232, an extension member 30, a first contact assembly 31, a first contact terminal 311, a first conductive terminal 312, a conductive paste 3121, a first connection portion 313, a second contact assembly 32, a second contact terminal 321, a second conductive terminal 322, a second connection portion 323, a detection apparatus 40, a wristband 41, and a receiving space 50.

Herein, example implementations or embodiments will be described in detail and illustrated in accompanying figures. When the following description refers to the accompanying figures, the same label in different figures represents the same or similar element unless indicated otherwise. The implementations described in examples do not represent all implementations that are consistent with this disclosure. Rather, they are merely example apparatuses and methods consistent with aspects of this disclosure as detailed in the appended claims.

The terms used herein are for the purpose of describing implementations only and are not intended to limit this disclosure. The singular forms "a," "an," and "the" used herein intend to include plural forms unless the context clearly indicates otherwise. It should also be understood that the term "and/or" as used herein refers to and encompasses any or all of one or more possible combinations of the associated listed items.

It should be understood that although the terms "first," "second," "third," etc. can be used to describe various kinds of information in this disclosure, the information should not be limited to these terms. These terms are only used to distinguish the same type of information from each other. For example, without departing from the scope of this disclosure, the first information can also be referred to as the second information. Similarly, the second information can also be referred to as the first information. Depending on the context, the word "if" as used herein can be interpreted as "when," "while," or "in response to."

A base and a detection device for installing a detection apparatus are provided in this disclosure. The detection apparatus can be disassembled from a wearable device and be installed onto the base member using a first fixing member so that the detection apparatus can form an integral structure with the base. An extension member can extend along a base member of the base to a predetermined position of the base member, so that the detection apparatus can obtain, by the extension member, an electric signal of a detection portion in contact with a predetermined position of an individual.

Figure 2:
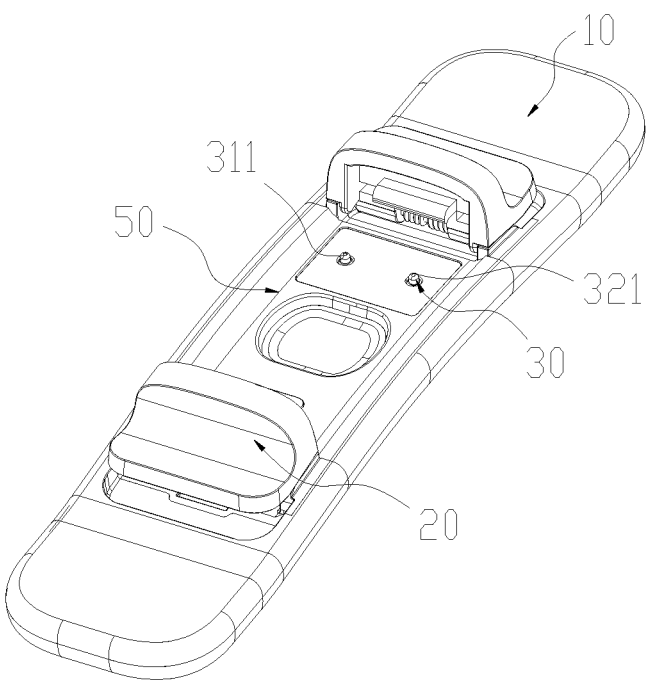
FIG. 2 is a diagram of structures of a base according to an implementation of this disclosure.
Figure 3:
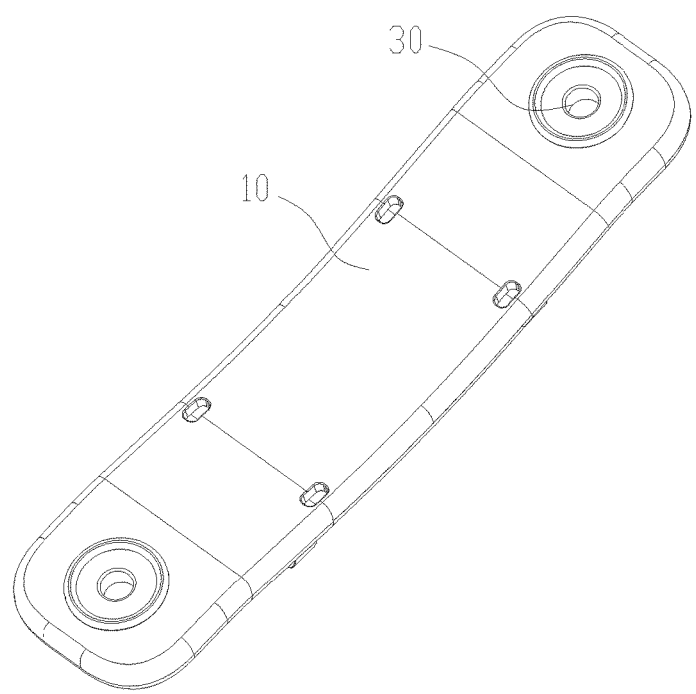
FIG. 3 is a diagram of structures of the base from another angle according to an implementation of this disclosure.

FIG. 1 is a diagram of structures of a detection device according to an implementation of this disclosure. FIG. 2 is a diagram of structures of a base according to an implementation of this disclosure. FIG. 3 is a diagram of structures of the base from another angle according to an implementation of this disclosure. As shown in FIGS. 1-3, the base is provided according to an implementation of this disclosure. The base can be used to install a preset detection apparatus 40. The base can include a base member 10, a first fixing member 20 set on the base member 10 for fixing the detection apparatus 40, and an extension member 30 for transmitting an electric signal to the detection apparatus 40. The extension member 30 can be extended to a predetermined position of the base member 10.

Figure 7:
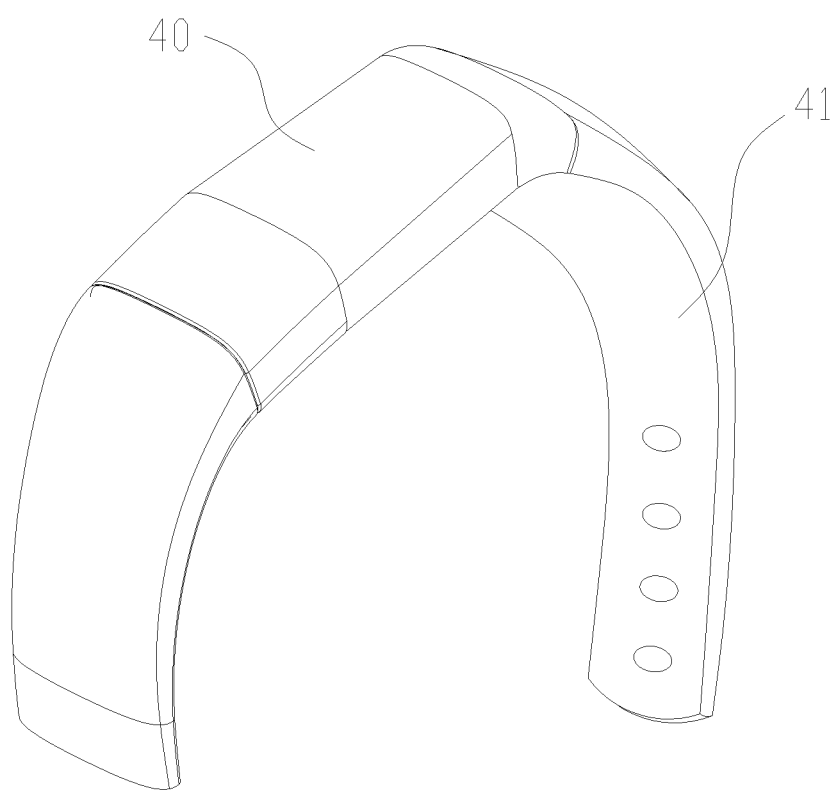
FIG. 7 is a diagram of structures of a wearable device according to an implementation of this disclosure.

In an implementation, the detection apparatus 40 can include a main portion, an installation portion located on the main portion, and a detection portion. The installation portion can be used to connect with an external component (e.g., a wristband). The detection portion can be used to receive the electric signal. The main portion can be used to output and display parameter information. FIG. 7 is a diagram of structures of a wearable device according to an implementation of this disclosure. A wristband 41 can be installed on installation portions at two ends of the main portion of the detection apparatus 40. Thus, the detection apparatus 40 and the wristband 41 can form the wearable device as shown in FIG. 7.

The base member 10 can have a coverage area greater than a coverage area of the detection apparatus 40. The base member 10 can also be used to install or mount the detection apparatus 40 to the base using the first fixing member 20 so that the detection apparatus 40 and the base can form an integrated structure. The extension member 30 can be extended to the predetermined position of the base member 10 along the base member 10. The detection apparatus 40 can obtain, through the extension member 30, an electric signal of a detection portion (e.g., a body part under detection) that contacts with the predetermined position, so that the detection apparatus 40 can meet a detection requirement.

In some implementations, when the detection apparatus 40 is detached from the wearable device, it can be used on the base. While satisfying the detection requirement of the wearable device, the detection apparatus 40 can also be combined with the base to form a detection device for a wide coverage area of detection, such as detection of an important body part (e.g., the heart). In this way, the detection apparatus can have a wide range of applications and be convenient to carry and use.

For example, the first fixing member 20 can form an integrated part with the base member 10, or be independently installed onto the base member 10. A receiving space for accommodating the detection apparatus 40 can be formed between the first fixing member 20 and the base member 10. In an implementation, the first fixing member 20 can protrude at least partially from the base member 10. The receiving space for accommodating the detection apparatus 40 can be formed between the first fixing member 20 and the base member 10. In another implementation, the first fixing member 20 can protrude at least partially from the base member 10. The detection apparatus 40 can be provided with a recessed portion matching with the first fixing member 20 so that the detection apparatus 40 can be fixed on the base member 10. In another implementation, the base member 10 can have a recessed portion to form the first fixing member 20, and a protruding portion can be provided with the detection apparatus 40 to match with the first fixing member 20. In another implementation, the detection apparatus 40 can be bonded (e.g., glued) onto the first fixing member 20 of the base member 10.

The detection apparatus 40 can be connected to the base via the above-mentioned ways. For ease of explanation, the description hereinafter will assume that the first fixing member 20 at least partially protrudes from the base member 10 and forms a receiving space between the first fixing member 20 and the base member 10 to accommodate the detection apparatus 40.

As shown in FIG. 2, in an implementation, the first fixing member 20 can protrude outward from the base member 10, forming a receiving space 50 between the first fixing member 20 and the base member 10.

In an implementation, the detection apparatus 40 and the base can be two independent parts. The receiving space 50 can be used to receive the detection apparatus 40.

In an implementation, the first fixing member 20 can be flexibly and annularly disposed on the base member 10. The receiving space 50 can form a counterbore-shaped structure. The detection apparatus 40 can be pressed by the first fixing member 20 against the base. The detection apparatus 40 can receive the electric signal from the extension member 30.

In another implementation, at least one fixing member can be installed on the base member 10. The at least one fixing member can fix the detection apparatus 40 by snapping, clamping, or gripping. For example, a first fixing member and a second fixing member can be provided on the base member 10 and be oppositely disposed.

Figure 4:
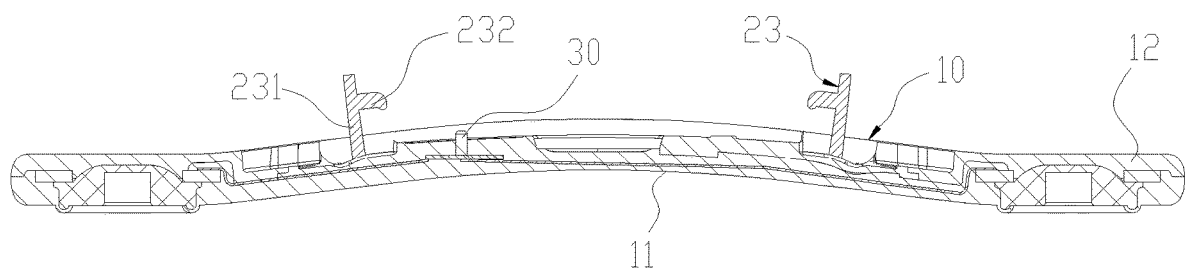
FIG. 4 is a cross-sectional diagram of a first fixing member according to an implementation of this disclosure.

FIG. 4 is a cross-sectional diagram of a first fixing member according to an implementation of this disclosure. As shown in FIG. 4, the first fixing member 20 can include a clip member 23 fixed to the base member 10. The clip member 23 can protrude from an upper surface of the base member 10. The clip member 23 can include an elastic portion 231 and a holding portion 232 on the elastic portion 231. The elastic portion 231 can be fixed to the base member 10 and generate an elastic force. The holding portion 232 can be used to hold (e.g., by snapping, clamping, or gripping) the detection apparatus 40. The elastic portion 231 can generate an elastic force so that the holding portion 232 can be caused to have a holding force for squeezing the receiving space 50 under the elastic force.

In an implementation, when two clip members 23 are oppositely arranged on the base member 10, the receiving space 50 can be formed between the two clip members 23 and the upper surface of the base member 10. The holding portion 232 can be located on the elastic portion 231. The detection apparatus 40 can be pressed against the clip member 23 along an opening of the receiving space 50 so that the elastic portion 231 can generate an elastic force. The holding portion 232 can generate the holding force for squeezing the receiving space 50 under the elastic force so that the detection apparatus 40 can be held by the holding portion 232.

By elastically holding the installation portion of the detection apparatus 40 using the clip member 23 provided on the base member 10, the installation of the detection apparatus 40 to the base can become more convenient. The clip member 23 and the base member 10 can form an integrated structure, which can be easy to manufacture, process, and use.

Figure 5:
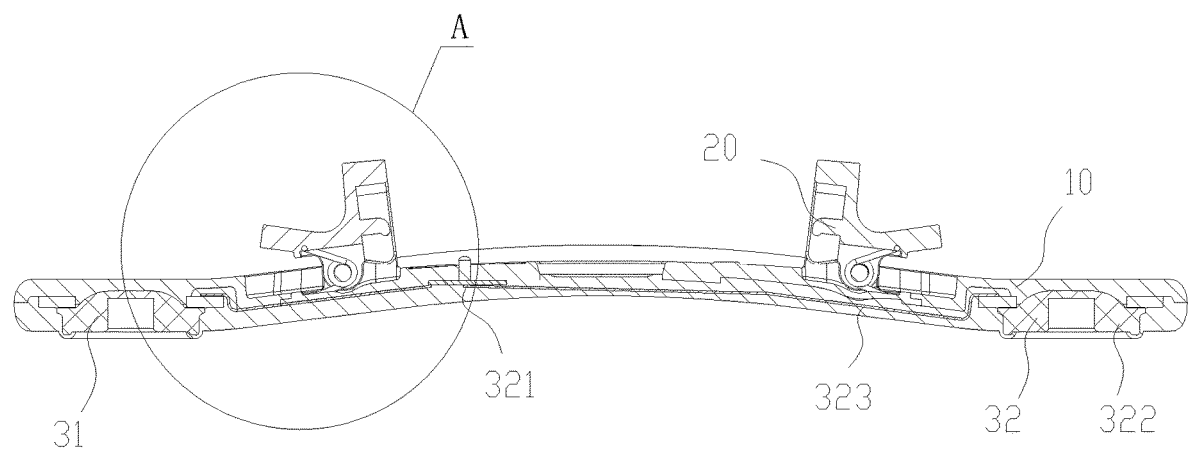
FIG. 5 is a cross-sectional diagram of another first fixing member according to an implementation of this disclosure.
Figure 6:
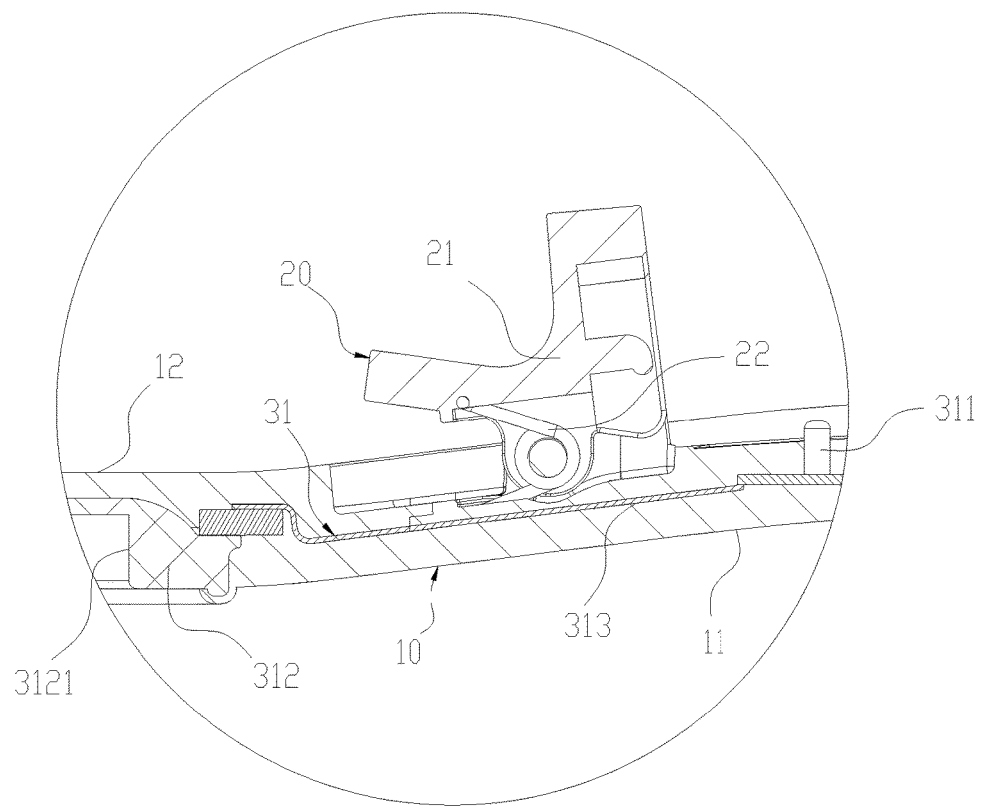
FIG. 6 is an enlarged diagram of structures of part A of FIG. 5.

FIG. 5 is a cross-sectional diagram of another first fixing member according to an implementation of this disclosure. FIG. 6 is an enlarged diagram of structures of part A of FIG. 5. As shown in FIGS. 5 and 6, the first fixing member 20 can include a clamp member 21 hinged onto the base member 10, and an elastic element 22 elastically contacting the clamp member 21. The elastic element 22 can be elastically deformed, such that the clamp member 21 can be caused to have a clamping force for squeezing the receiving space 50. The clamp member 21 can be used to hold the detection apparatus 40.

In some implementations, the first fixing member 20 can be assembled with the base member 10. The clamp member 21 can be configured to rotate about the hinge point on the base member 10. The elastic element 22 can be elastically pressed against the clamp member 21 so that the clamp member 21 and the base member 10 can form a clamping structure. In an implementation, the elastic element 22 can be a compression spring or a torsion spring.

In an implementation, when a first holding member and a second holding member are provided and oppositely disposed on the base member 10, the receiving space 50 can be formed between the first fixing member, the second fixing member, and the upper surface of the base member 10. When the clamp member 21 rotates around the hinge point, the receiving space 50 can be formed between the clamp member 21 and the base member 10. The detection apparatus 40 can be installed in the receiving space 50. When the clamp member 21 is loosened, the clamp member 21 can press the installation portion of the detection apparatus 40 under the action of the elastic force, so that the detection apparatus 40 can be fixed to the base member 10.

As shown in FIGS. 5 and 6, in an implementation, the extension member 30 can include a first contact assembly 31 and a second contact assembly 32. The first contact assembly 31 and the second contact assembly 32 can extend outward from the receiving space 50.

The extension member 30 can be used to transmit the electric signal from the detection portion to the detection apparatus 40. Because the coverage area of the extension member 30 for receiving the electric signal is larger than the coverage area of the detection apparatus 40 for receiving the electric signal, a first contact terminal 311 of the first contact assembly 31 and a second contact terminal 321 of the second contact assembly 32 can be located within the receiving space 50 and respectively connected to two detection portions of the detection apparatus 40. A first conductive terminal 312 of the first contact assembly 31 and a second conductive terminal 322 of the second contact assembly 32 can be respectively extended outward from the receiving space 50, causing the detection apparatus 40 to have an effectively larger detection coverage area. For example, the first contact assembly 31 and the second contact assembly 32 can be extended in different directions along the base member 10.

In an implementation, the first contact assembly 31 can include the first contact terminal 311, a first conductive terminal 312, and a first connection portion 313 connecting the first contact terminal 311 and the first conductive terminal 312. The second contact assembly 32 can include the second contact terminal 321, a second conductive terminal 322, and a second connection portion 323 connecting the second contact terminal 321 and the second conductive terminal 322. The first contact terminal 311 and the second contact terminal 321 can be located within the receiving space 50 for conducting with the detection apparatus 40. The first conductive terminal 312 and the second conductive terminal 322 can be used for receiving the electric signal from the detection portion.

The first contact terminal 311 and the second contact terminal 321 can partially protrude from an outer surface of the base member 10 so that the first contact terminal 311 and the second contact terminal 321 can be in close contact with a detecting part of the detection apparatus 40. In an implementation, the first contact terminal 311 and the second contact terminal 321 can be provided as an elastic telescopic structure, which can improve the stability and the electrical conductivity between the first contact terminal 311, the second contact terminal 321, and the detecting part of the detection apparatus 40.

In an implementation, the first connection portion 313 and/or the second connection portion 323 can be arranged within base member 10 and extend outward from the receiving space 50. The first conductive terminal 312 and the second conductive terminal 322 can be provided with a conductive paste 3121. The conductive paste 3121 can partially protrude from the surface of the base member 10.

The first connection portion 313 and the second connection portion 323 can be arranged within the base member 10, so that the extension member 30 and the base member 10 can form an integrated structure, which can provide easy manufacturing and processing. The conductive paste 3121 can protrude from the surface of the base member 10. When the base is attached to the skin of an individual, the conductive paste 3121 can be pressed and adhered to the skin with good conductivity and easy attachment.

In an implementation, the first connection portion 313 and the second connection portion 323 can extend outward from the base member 10. The first connection portion 313 and the second connection portion 323 can protrude from the base member 10 in a line shape. The first conductive terminal 312 can be disposed at an end of the first connection portion 313. The second conductive terminal 322 can be disposed at an end of the second connection portion 323. The first conductive terminal 312 and the second conductive terminal 322 can be provided with the conductive paste 3121 that can be adhered to a skin surface, which can cause the detection apparatus 40 to be easy to operate and have a greater attachment range and a higher degree of freedom.

As shown in FIGS. 4-6, in an implementation, the base member 10 can include an arcuate portion 11 and contact portions 12 respectively located at a first end and a second end of the arcuate portion 11. The extension member 30 can be connected to the contact portion 12 by extending through the arcuate portion 11. In an implementation, the first fixing member 20 can be installed on the arcuate portion 11. For example, the arcuate portion 11 can have an arc shape, and the contact portions 12 located at the first end and the second end of the arcuate portion 11 can be in the same plane.

In a case where the base member 10 has a plate-like structure, the contact portions 12 can protrude from a surface of the arcuate portion 11, so that a contact surface of the base member 10 with the skin can be reduced. Thus, the extension member 30 connected to the contact portion 12 can better contact with the skin of the detection portion. When the arcuate portion 11 is set as the arc shape, and when the base is attached to the skin surface, the arcuate portion 11 can be pressed to be flexed and generate an elastic stress to ensure that the extension member 30 connected to the contact portion 12 can be closely attached to the skin.

It should be noted that the base as disclosed herein can be matched with the detection apparatus 40 that can be installed on a wearable device and form a detection device. Meanwhile, for example, after being detached from the base, the detection apparatus 40 can be combined with the wristband 41 to form the wearable device. By being combined with the wristband or the base, the detection apparatus 40 can achieve interchangeable application between the wearable device and the detection device.

The above description includes merely example implementations of the present disclosure and is not intended to limit the present disclosure. Any modification, equivalent substitution, and improvement made within the spirit and principles of the present disclosure shall be deemed as falling into the protection scope of the present disclosure.

What is claimed is:

1. A base for installing a detection apparatus, comprising:
a base member comprising a length and at least one contact portion;
a first fixing member, provided on the base member for fixing the detection apparatus;
a receiving space defined along the base member that is configured to receive the detection apparatus, wherein the at least one contact portion extends away from the receiving space in a longitudinal direction corresponding to the length; and
an extension member, configured to transmit an electric signal to the detection apparatus, wherein the extension member extends outward from the receiving space to the at least one contact portion of the base member.

2. The base of claim 1, wherein the receiving space is formed between the first fixing member and the base member.

3. The base of claim 2, wherein at least a portion of the first fixing member protrudes outward from the base member.

4. The base of claim 2, wherein the extension member comprises a first contact assembly and a second contact assembly, and the first contact assembly and the second contact assembly extend outward from the receiving space.

5. The base of claim 4, wherein
the first contact assembly comprises a first contact terminal, a first conductive terminal, and a first connection portion connecting the first contact terminal and the first conductive terminal,
the second contact assembly comprises a second contact terminal, a second conductive terminal, and a second connection portion connecting the second contact terminal and the second conductive terminal,
the first contact terminal and the second contact terminal are inside the receiving space and configured to conduct the detection apparatus, and
the first conductive terminal and the second conductive terminal are configured to receive the electric signal.

6. The base of claim 5, wherein the first connection portion and the second connection portion are received inside the base member and extend outward from the receiving space.

7. The base of claim 5, wherein the first conductive terminal and the second conductive terminal are provided with a conductive paste, and the conductive paste partially protrudes out of a surface of the base member.

8. The base of claim 1, wherein the first fixing member comprises:
an elastic portion fixed to the base member; and
a holding portion provided on the elastic portion, wherein the elastic portion generates an elastic force to cause the holding portion to hold the detection apparatus under the elastic force.

9. The base of claim 1, wherein the first fixing member comprises:
a clamp member hinged to the base member; and
an elastic element elastically contacting the clamp member, wherein the elastic element elastically deforms to cause the clamp member to hold the detection apparatus.

10. The base of claim 1, further comprising:
a second fixing member, arranged on the base member opposing the first fixing member.

11. The base of claim 1, wherein:
the base member further comprises arcuate portion;
the at least one contact portion comprises a first contact portion and a second contact portion;
the first contact portion is provided at a first end of the arcuate portion;
the second contact portion is provided at a second end of the arcuate portion; and
the extension member extends to the first contact portion and the second contact portion from the arcuate portion.

12. The base of claim 11, wherein the arcuate portion is in an arc shape, and the first contact portion and the second contact portion are on the same plane.

13. A detection device, comprising:
a detection apparatus; and
a base, wherein the base comprises:
a base member;
a first fixing member, provided on the base member for fixing the detection apparatus;
a receiving space formed between the base member and the first fixing member that is configured to receive the detection apparatus, wherein the receiving space defines a receiving area on the base member; and
an extension member, configured to transmit an electric signal to the detection apparatus, wherein the extension member extends outward from the receiving space to a predetermined position of the base member located outboard of the receiving area.

14. The detection device of claim 13, wherein the detection apparatus is detachable from the detection device at the receiving space and attachable to a wearable device.

15. The detection device of claim 13, wherein the first fixing member comprises:
an elastic portion fixed to the base member; and
a holding portion provided on the elastic portion, wherein the elastic portion generates an elastic force to cause the holding portion to hold the detection apparatus under the elastic force.

16. The detection device of claim 13, wherein the first fixing member comprises:
a clamp member hinged to the base member; and
an elastic element elastically contacting the clamp member, wherein the elastic element elastically deforms to cause the clamp member to hold the detection apparatus.

17. A detection device, comprising:
a detection apparatus;
a wristband; and
a base, wherein the base comprises:
a base member including contact portions;
a first fixing member, provided on the base member for fixing the detection apparatus;
a receiving space formed between the first fixing member and the base member for receiving the detection apparatus, the receiving space having a length; and an extension member, configured to transmit an electric signal to the detection apparatus, wherein a distance between the contact portions of the base member is greater than the length of the receiving space, and the extension member extends outward from the receiving space to the contact portions of the base member.

18. The detection device of claim 17, wherein the detection apparatus is detachable from the detection device at the receiving portion and attachable to a wearable device.

19. The detection device of claim 17, wherein the first fixing member comprises:
- an elastic portion fixed to the base member; and
- a holding portion provided on the elastic portion, wherein the elastic portion generates an elastic force to cause the holding portion to hold the detection apparatus under the elastic force.

20. The detection device of claim 17, wherein the first fixing member comprises:
- a clamp member hinged to the base member; and
- an elastic element elastically contacting the clamp member, wherein the elastic element elastically deforms to cause the clamp member to hold the detection apparatus.

\* \* \* \* \*